US00RE37977E

(19) United States
(12) Reissued Patent
Sugihara et al.

(10) Patent Number: US RE37,977 E
(45) Date of Reissued Patent: Feb. 4, 2003

(54) CELL POTENTIAL MEASURING ELECTRODE AND MEASURING APPARATUS USING THE SAME

(75) Inventors: Hirokazu Sugihara, Osaka (JP); Hiroaki Oka, Osaka (JP); Ken Shimono, Irvine, CA (US); Ryuta Ogawa, Osaka (JP); Makoto Taketani, Irvine, CA (US)

(73) Assignee: Matsushita Electric Industrial Co., Ltd., Osaka (JP)

(21) Appl. No.: 09/953,412

(22) Filed: Sep. 11, 2001

Related U.S. Patent Documents

Reissue of:
(64) Patent No.: 6,132,683
Issued: Oct. 17, 2000
Appl. No.: 09/220,981
Filed: Dec. 23, 1998

(30) Foreign Application Priority Data

Dec. 25, 1997 (JP) ..... 9-358601

(51) Int. Cl.[7] ..... G01N 27/00; G01N 27/403; G01N 27/327

(52) U.S. Cl. ..... 422/82.01; 204/403.01; 204/403.13; 204/412

(58) Field of Search ..... 204/403.01, 403.13, 204/412; 422/82.01

(56) References Cited

U.S. PATENT DOCUMENTS 5,187,096 A * 2/1993 Giaever et al. ..... 204/403.01
5,563,067 A * 10/1996 Sugihara et al. ..... 204/403.01
5,810,725 A * 9/1998 Sugihara et al. ..... 204/403.01

FOREIGN PATENT DOCUMENTS

DE 19529371 A1 * 2/1997
EP 0689051 A3 * 12/1995
EP 0823483 A1 * 2/1998
JP 08-62209 * 3/1996
WO 98/54294 * 12/1998

OTHER PUBLICATIONS

P. 39 of Davies et al. ("A Dictionary of Electrochemistry", John Wiley & Sons, NY, 1976).*

Hinkers, H. et al. (1995), "An amperometric microsensor array with 1024 individually addressable elements for two–dimensional concentration mapping" Sensors Actuators B 24–25, 300–303, month unknown 1995.*

Kordas, N. et al. (1994), month unknown "a CMOS–compatible monolithic conductivity sensor with integrated electrodes," Sensors Actuators a, 43 Nos. 1/3, 31–37.*

Mohr, A et al. (1996), month unknown "Performance of a thin film microelectrode for monitoring electrogenic cells in vitro," Sensors actuators B 34, 265–269.*

* cited by examiner

*Primary Examiner*—T. Tung
*Assistant Examiner*—Alex Noguerola
(74) *Attorney, Agent, or Firm*—Morrison & Foerster LLP

(57) ABSTRACT

This invention relates to a low impedance cell potential measuring electrode assembly typically having a number of microelectrodes on an insulating substrate and having a wall enclosing the region including the microelectrodes. The device is capable of measuring electrophysiological activities of a monitored sample using the microelectrodes while cultivating those cells or tissues in the in the region of the microelectrodes. The invention utilizes independent reference electrodes to lower the impedance of the overall system and to therefore lower the noise often inherent in the measured data. Optimally the microelectrodes are enclosed by a physical wall used for controlling the atmosphere around the monitored sample.

24 Claims, 10 Drawing Sheets

CELL POTENTIAL MEASURING ELECTRODE AND MEASURING APPARATUS USING THE SAME

Matter enclosed in heavy brackets [ ] appears in the original patent but forms no part of this reissue specification; matter printed in italics indicates the additions made by reissue.

FIELD OF THE INVENTION

This invention relates to a low impedance cell potential measuring electrode assembly typically having a number of microelectrodes on an insulating substrate and having a wall enclosing the region including the microelectrodes. The device is capable of measuring electrophysiological activities of a monitored sample using the microelectrodes while cultivating those cells or tissues in the in the region of the microelectrodes. The invention utilizes independent reference electrodes to lower the impedance of the overall system and to therefore lower the noise often inherent in the measured data. Optimally the microelectrodes are enclosed by a physical wall used for controlling the atmosphere around the monitored sample.

BACKGROUND OF THE INVENTION

Cell potential measuring apparatus have been developed to measure the activity or electrical potential generated by activity of nerve cells, other cells, or tissues (for example, Japanese Kokai 8-62209) without inserting glass electrodes or the like into the cells.

Measurement of cell potential by inserting a glass electrode or the like into the cell may damage that cell. Long term measurement of cell potential is quite difficult. It is further difficult to measure plural positions simultaneously; there is a limit to the number of electrodes one can place in a measurement electrode array and it is similarly difficult to adequately determine the position of the sample over measurement electrodes. In contrast, use of a cell potential measuring electrode having plural microelectrodes on a substrate (having a wall for enclosing a region including the microelectrodes), allows cultivation of the cells within the region enclosed by the wall and the simultaneous measurement of the potential of plural positions without damaging those cells.

These cell potential measuring devices measures cell potential against a reference. One such way is discussed with regard to Kokai 8-62209. When 64 microelectrodes are arranged in eight columns and eight rows, theoretically, by using one microelectrode as the reference potential (that is, as a common reference electrode connected to the potential of the culture medium) the cell potential of the other 63 positions can be measured simultaneously by using the remaining 63 microelectrodes.

However, when measuring very low level or micropotentials such as cell potentials, noise is a problem. Noise level varies significantly depending on the selection of the type and location of the reference electrode. As mentioned above, when using one microelectrode as a reference electrode, simultaneous measurement of potential at 63 positions by using the remaining 63 microelectrodes is impossible because of the high noise level. When the reference electrodes and measuring electrodes correspond one-by-one to each other, the potential may be measured at a very low noise level state; But if 64 microelectrodes are used, for example, corresponding to 32 reference electrodes and 32 measuring electrodes, only 32 positions can be measured simultaneously.

In theory, though, one must limit the number of reference electrodes in order to simultaneously measure the potential at as many positions as possible.

As shown in FIG. 12, eight microelectrodes in one row are used as reference electrodes and seven measuring electrodes each are correlated to each of the reference electrodes, so that the potential can be measured simultaneously at 7×8=56 positions. If 56 microelectrodes are used as measuring electrodes, i.e., by using eight microelectrodes in one row as reference electrodes, the loss of measuring sites is about 12% as compared with the case of using all 64 or 63 pieces as measuring electrodes. However, even when seven measuring electrodes are used with one reference electrode, the noise is still quite large. It is quite difficult to detect a small change in cell potential from the noise.

Moreover, as shown in FIG. 12, when placing a segment S of cell or tissue on the plural microelectrodes, the segment S should not be placed on the row of microelectrodes used as reference electrodes. Such a placement requires skill and is difficult because the segment S must be held by tweezers and moved while observing the segment through a microscope. It is extremely difficult to place the segment S so that the eight microelectrodes in one row are completely exposed, while the remaining 56 microelectrodes be completely covered with the segment. If the segment S is placed to completely expose the eight microelectrodes in one row, usually some of the remaining 56 are exposed, and hence the number of positions for simultaneous measurement is decreased.

SUMMARY OF THE INVENTION

The invention is intended to solve such problems. This invention provides a cell potential measuring electrode less susceptible to noise and is yet capable of simultaneously measuring the potential at many positions by effectively utilizing all of the available microelectrodes if the positioning is not very precise when placing the segment of cell or tissue to be measured.

The cell potential measuring electrode of the invention preferably includes plural microelectrodes on an insulating substrate, a conductive pattern for connecting the microelectrodes to some region out of the microelectrode are, electric contacts connected to the end of the conductive pattern, an insulating film covering the surface of the conductive pattern, and a wall enclosing the region including the microelectrodes on the surface of the insulating film. The inventive reference electrodes have a comparatively lower impedance than the impedance of the measuring microelectrodes. They are respectively placed at plural positions in the region enclosed by the wall and often at a specific distance from the microelectrodes. The electrical contacts are further usually connected between the conductive pattern for wiring of each reference electrode and the end of the conductive pattern. The surface of the conductive pattern for wiring of the reference electrodes is typically covered with an insulating film.

According to this invention, since exclusive reference electrodes are provided at plural positions distant from the region of plural measurement microelectrodes, it is easy to place the segment of cell sample to cover all microelectrodes while not contacting with the reference electrodes. The reference electrode would typically have, for example, a larger area than a measurement microelectrodes and hence is smaller in impedance. Therefore the noise level is small even if connected to plural reference potentials for measuring positions. Therefore, common reference electrodes can be used with multiple measurement microelectrodes. Moreover, since each one of the plural reference electrodes is responsible for multiple measurement microelectrodes, the cell potentials may be easily measured simultaneously using all of microelectrodes.

Preferably, the plural reference electrodes are placed at nearly equal distances from the plural microelectrode region and at intervals of nearly equal angle. By "intervals of nearly equal angle", we mean that when the plural microelectrode region is viewed from above, the plural reference electrodes extend away from that region in equi-angular rays. More preferably, the plural microelectrodes are placed in a rectangular matrix, and four of the reference electrodes are provided on an extension of diagonals of the region holding that rectangular matrix. In such a symmetrical placement, the noise level to each microelectrode is averaged.

As a specific example, the microelectrodes are situated in a matrix arrangement in a rectangle having sides of, e.g., 0.8 to 2.2 mm (in the case of 450 $\mu$m microelectrode pitch) or 0.8 to 3.3 mm (in the case of 300 $\mu$m microelectrode pitch). Four reference electrodes are situated at four corners of a rectangle of 5 to 15 mm on one side. More preferably, 64 microelectrodes are disposed in eight rows and eight columns at central pitches of about 100 to 450 $\mu$m, preferably 100 to 300 $\mu$m.

In order to set the impedance of the reference electrodes to be sufficiently smaller than the impedance of the microelectrodes, the area of the reference electrodes is preferably 4 to 25 times (particularly preferably 16 times) the area of the microelectrodes. As a specific example, the area of each of the microelectrodes is preferably between about $4\times10^2$ and $4\times10^4$ $\mu m^2$ and the area of each of the reference electrodes is preferably between about $64\times10^2$ and $64\times10^4$ $\mu m^2$.

Preferably the microelectrodes and the reference electrodes are formed from the same material to both simplify the manufacturing process and obtain a cost benefit. Preferably, the microelectrodes and the reference electrodes are formed of layers of nickel plating, gold plating, and platinum black on an indium-tin oxide (ITO) film. After platinization, the impedance of the reference electrodes is preferably between 2 and 3 kilohms.

The insulating substrate (for example, a glass substrate) may be nearly square. Plural electric contacts may be connected to the end of the conductive pattern and preferably are placed on the four sides of the insulating substrate. As a result, layout of wiring patterns of multiple microelectrodes and reference electrodes is easy. Because the pitches of electric contacts may be made to be relatively large, electric connection through the electric contacts with external units is also easy.

The microelectrode region is usually very small. When observing the sample through a microscope, it is hard to distinguish position and both vertical and lateral directions. It is desirable to place indexing micro-marks near the microelectrode region to allow visual recognition through the microscope variously of direction, axes, and position.

The most preferred cell potential measuring apparatus of this invention is made up of a cell placement device having cell potential measuring electrodes, contact sites for contacting with an electric contact, and an electrode holder for fixing the insulating substrate by sandwiching from above and beneath. In a variation of the invention, a signal processor may be placed near the microelectrode matrix or region. The cell potential measuring electrodes may be connected electrically to the cell placement assembly device to allow processing of the voltage signals generated by the sample and measured between each such microelectrode and the reference electrodes. The cell potential measuring assembly usually includes a region enclosed by a wall for cultivating sample cells or tissues. It also preferably includes an optical device for magnifying and observing optically the cells or tissues cultivated in the region enclosed by the wall. This cell potential measuring apparatus preferably further comprises an image memory device for storing the magnified image obtained by the optical device.

DESCRIPTION OF THE INVENTION

Figure 1:
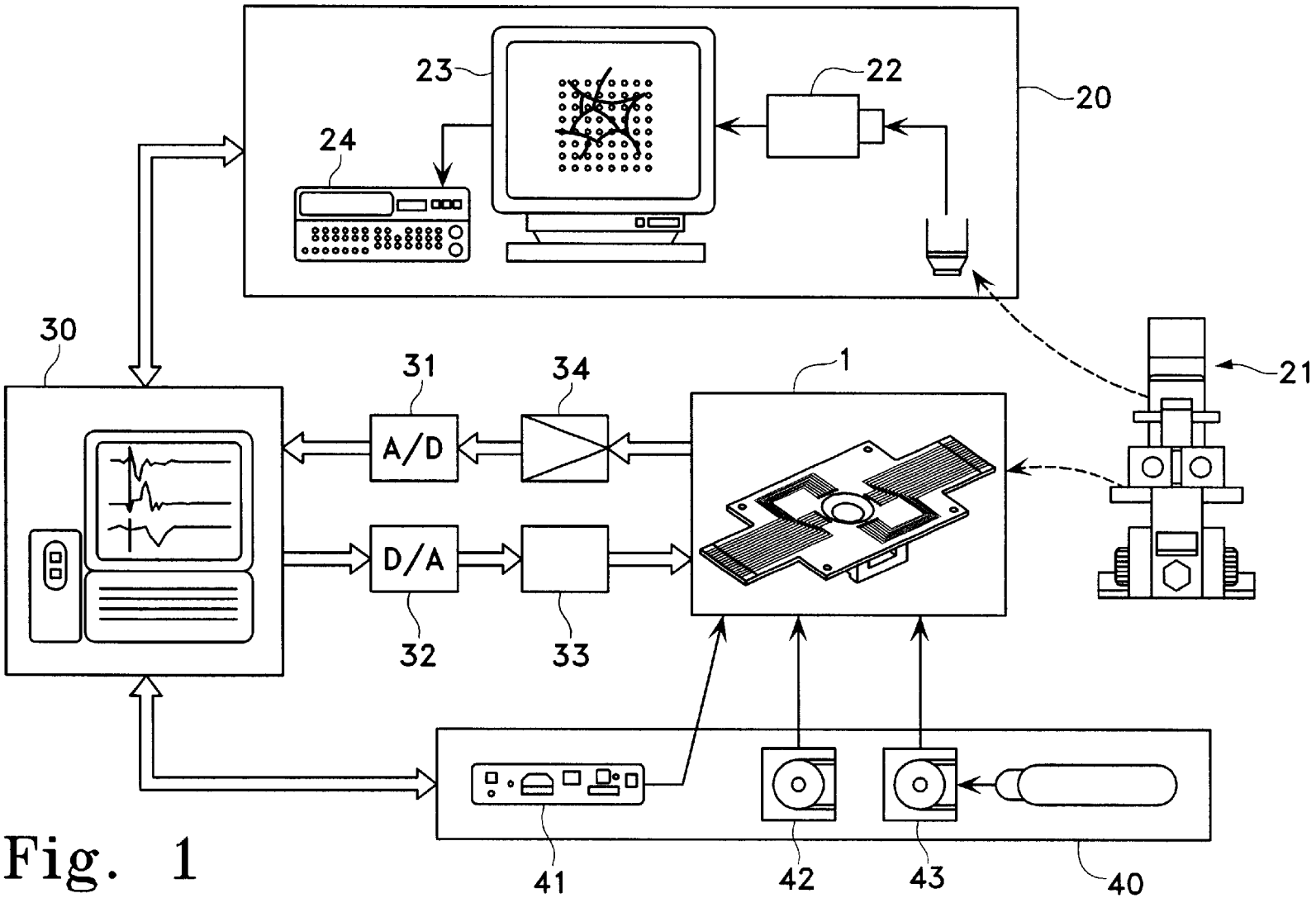
FIG. 1 is a block diagram showing an entire structure of a cell potential measuring apparatus according to the invention.

FIG. 1 shows a typical example of an entire cell potential measuring apparatus using a cell potential measuring electrode and reference electrode made according to the invention. This cell potential measuring apparatus comprises an integrated cell placement device 1 containing the cell potential measuring electrode of the invention, an optical observation device 20 including an inverted microscope 21 for optically measuring the sample or cells placed in the cell placement device 1, a computer 30 for giving a stimulus signal to the cells and for processing the output signal from the cells, and a cell culture system 40 for maintaining a culture atmosphere about the sample.

In addition to the inverted microscope 21 upon which the cell placement device 1 is set, the optical observation device 20 may also comprise an SIT camera 22 for the microscope 21, a high definition display 23, and an image memory device 24. The high definition display 23 may be also used as the display for the computer 30.

The computer 30 usually is a personal computer (PC) in which measurement software is installed. The computer 30 and cell placement device 1 are connected through an I/O board for measurement. The I/O board includes an A/D converter 31 and a D/A converter 32. The A/D converter 31 is usually for measuring and converting the resulting potentials; the D/A converter 32 is for stimulus signals to the sample. For example, the A/D converted 31 may have 16 bits, 64 channels, and the D/A converter 32 has 16 bits, 8 channels.

The measurement software installed in the computer 30 may include software for setting conditions for giving a stimulus signal, forming the stimulus signal, and for recording the obtained detection signal. By using such measurement software, the computer 30 may comprise means for giving a stimulus signal to the cells and means for processing the signal detected from the cells. The computer 30 may also control the optical observation device (SIT camera and image memory device) and the cell culture system.

An outline of the functionality of the desirable measurement software is described below screen-by-screen.

On a parameter setting screen, complicated stimulus conditions may be set by drawing a stimulus waveform on the screen by using a keyboard or a mouse. If a setting of recording condition is 64 input channels and a sampling rate of 10 kHz, the computer can handle consecutive recording for several hours. Moreover, electrodes to apply a stimulus signal and electrodes to pick up the detection signal from the cells can be designated by pointing out the microscope images displayed on the screen by the mouse or pen. The temperature, pH, and other conditions of the cell culture system 40 are desirably set from the keyboard.

On a recording screen, the spontaneous activity potential or induced potential detected from the cells may be displayed in real time. In addition, the recorded spontaneous activity, potential or induced potential can be displayed by overlaying on the microscope image of the cell. When measuring the induced potential, the entire recorded waveform is displayed. When measuring the spontaneous activity potential, by the spike detection function using window discriminator or waveform discriminator, the recorded waveform is displayed only when generation of spontaneous activity is detected. Together with the display of recorded waveform, measurement parameters (e.g., stimulus condition, recording conditions, temperature, pH, etc.) may also be displayed in real time. An alarm function is also provided for warning when the temperature or pH goes out of the allowable range.

Concerning data analysis or processing, Fourier Function Transform (FFT) analysis, coherence analysis, and correlation analysis are also desirable. Usable functions may include single spike separation function using waveform discrimination, temporal profile display function, topography display function, and current source density analysis function. These analysis results may be displayed by overlaying on the microscope images stored in the image memory devices.

When a stimulus signal is issued from the computer 30, this stimulus signal is sent to the cell placement device through the D/A converter 32 and an isolator 33. The cell placement device 1 includes a cell potential measuring electrode which may be formed, as described later, of 64 microelectrodes on a glass substrate in a matrix form and having an enclosing wall for maintaining the sample (e.g., segments of cells or tissues) in contact with the microelectrodes and their culture fluid. The stimulus signal sent to the cell placement device 1 is applied to arbitrary electrodes out of the 64 microelectrodes and then to the sample or samples.

The induced, evoked, or spontaneous potential occurring between each microelectrode and reference potential (which is at the potential of the culture fluid) is passed through a 64 channel high sensitivity amplifier 34 and the A/D converter 31 into the computer 30. The amplification factor of the amplifier 34 may be, e.g., about 80–100 dB, for example, in a frequency band of about 0.1 to 10 kHz, or to 20 Hz. However, when measuring the potential induced by a stimulus signal, by using a low-cut filter, the frequency band is 100 Hz to 10 kHz. Spontaneous potentials are usually in the range of 100 Hz to 20 Hz.

The cell culture system 40 usually includes a temperature controller 41, a culture fluid circulation device 42, and a feeder 43 for supplying, e.g., a mixed gas of air and carbon dioxide. The cell culture system 40 may instead be made up of a commercial microincubator, a temperature controller, and $CO_2$ cylinder. The microincubator can be used to control in a temperature range of 0 to 50° C. by means of a Peltier element and is applicable to the liquid feed rate of 3.0 ml/min or less and gas flow rate of 1.0 liter/min or less. Or, a microincubator incorporating a temperature controller may be used.

Figure 2:
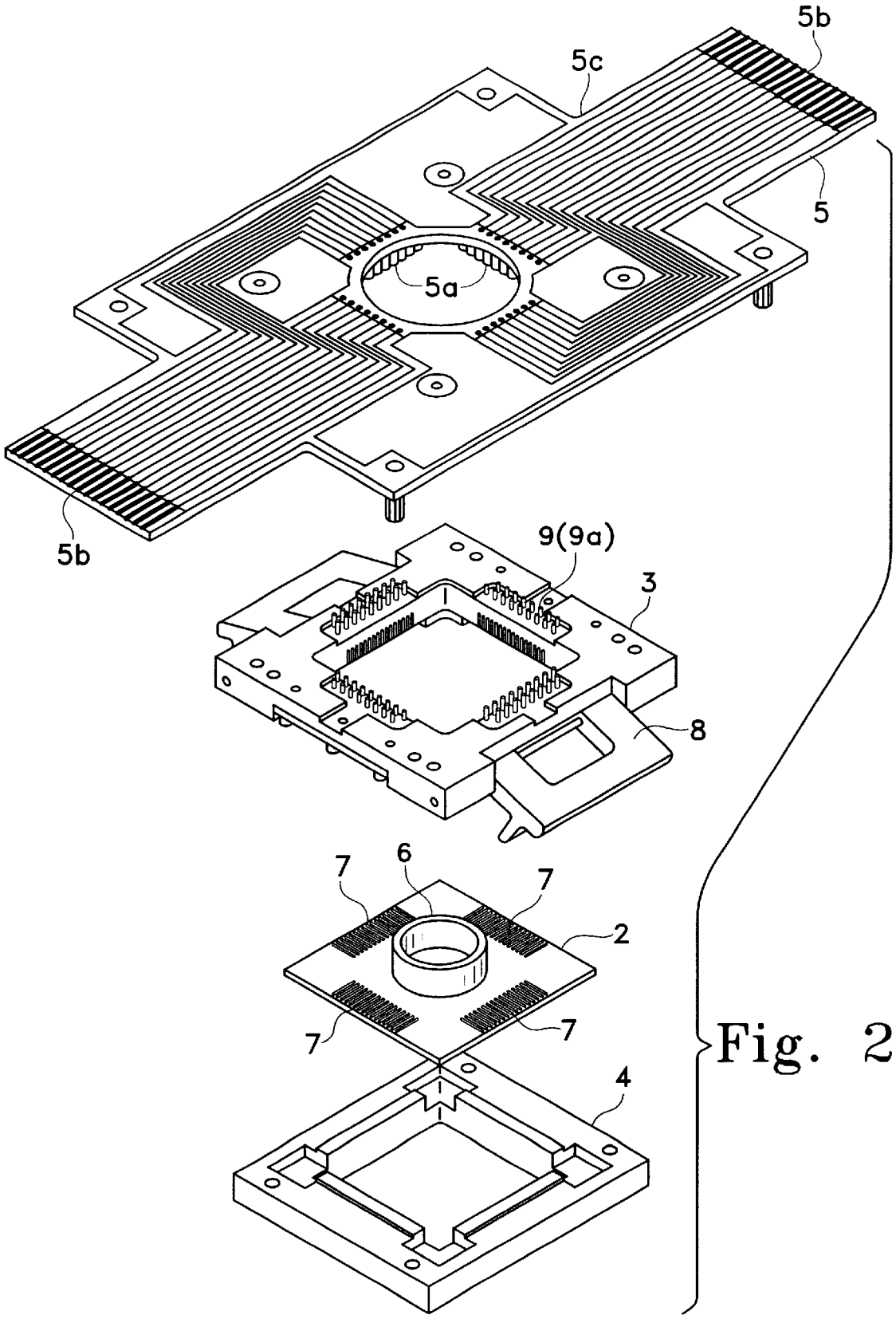
FIG. 2 is an exploded view of a cell placement device including the cell potential measuring electrode of the invention.

The structure of the cell placement device 1 (shown in FIG. 1) is explained in more detail with regard to the exploded view found in FIG. 2. The preferred cell placement device 1 may be made up of a cell potential measuring electrode (also called an integrated multiple electrode or microelectrode assembly) 2 having a cylindrical wall 6 provided on a transparent glass substrate and having plural microelectrodes in its inside region, holders 3, 40 divided in two sections for fixing the cell potential measuring electrode 2 by sandwiching from above and beneath, and a printed wiring board 5 for fixing the holders.

Figure 3:
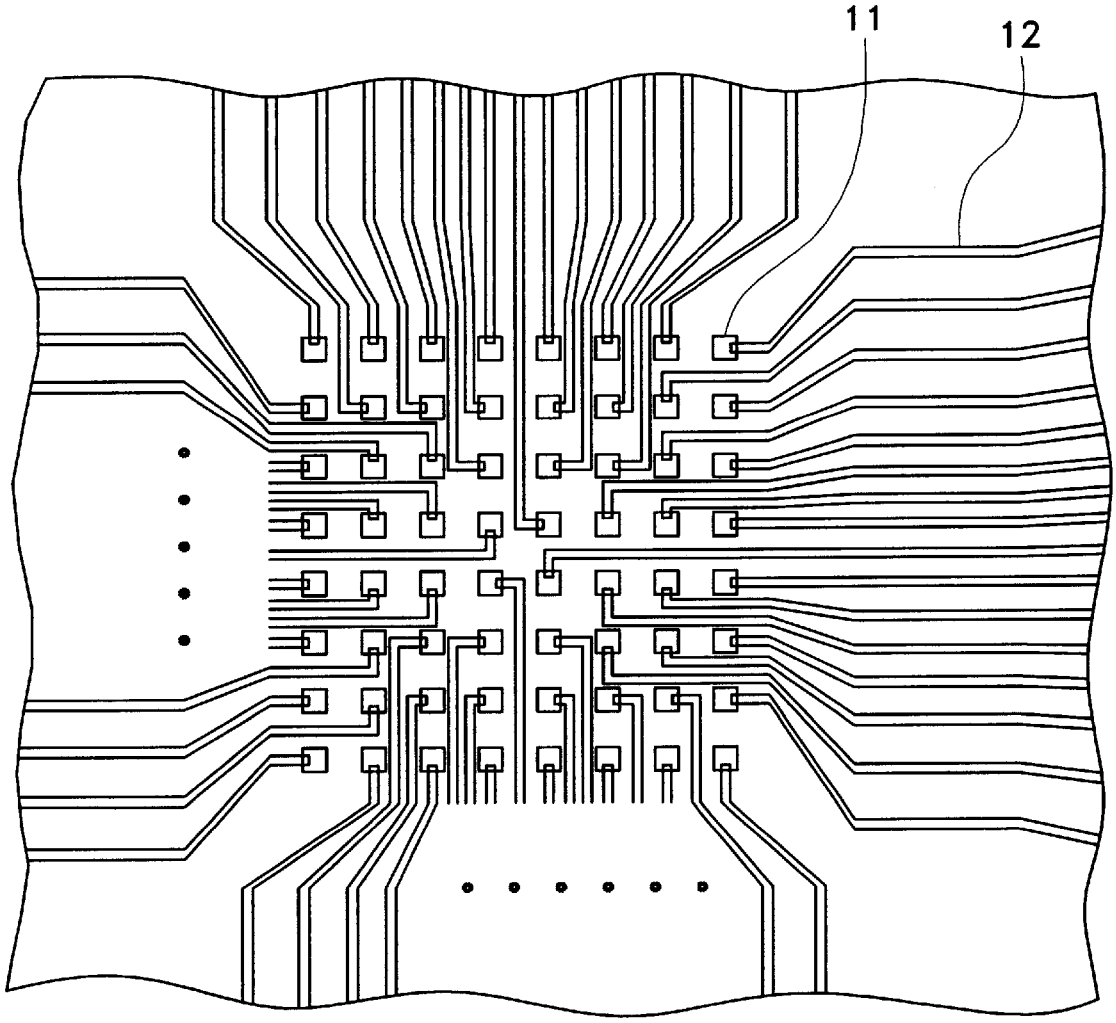
FIG. 3 is a partial plan view showing an example of microelectrodes in the central part of the cell potential measuring apparatus and a conductive pattern for its wiring.

FIG. 3 shows the details of the glass substrate. The size of the glass substrate for constituting the cell potential measuring electrode (integrated multiple electrode) 2 may be 1.1 mm in thickness and about 50 mm square. In the central part of the glass substrate, 64 microelectrodes 11 are formed in a matrix form of 8×8. The microelectrodes are insulated from each other and from the reference electrodes. A conductive pattern 12 for wiring is connected to each microelectrode 11. The microelectrode 11 may be about 50 microns square and the distance between centers of adjacent electrodes is about 150 microns. The depicted 64 microelectrodes 11 are therefore shown in a matrix form of 8×8, one side of the formed rectangular region is about 1.1 mm.

Although the Description of the Invention contains many specific references in particular sizes and areas, the invention is not so limited; they are only provided for the sake of guidance and are not critical to the invention unless so stated.

Figure 4:
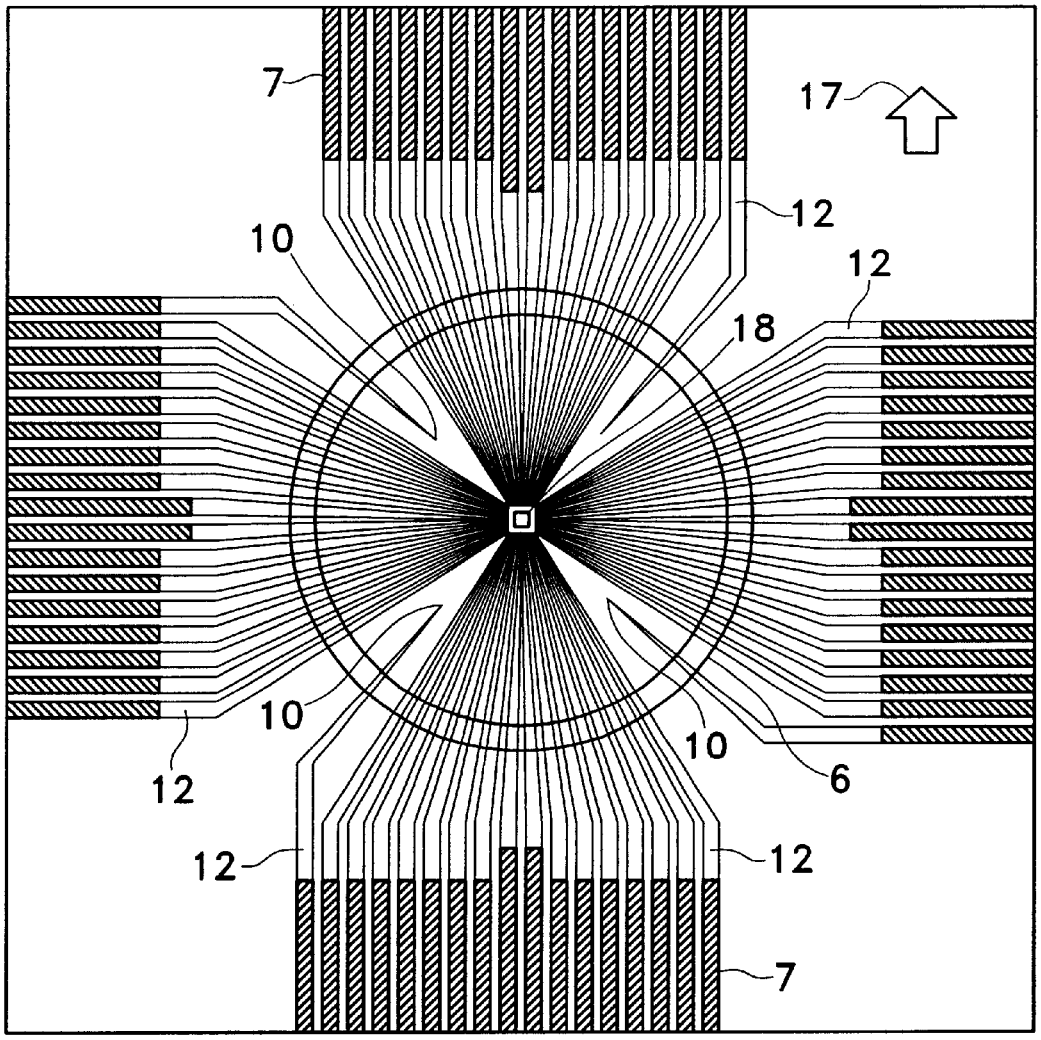
FIG. 4 is a plan view showing an entire structure of a cell potential measuring electrode.

Also, as shown in FIG. 4, reference electrodes 10 are formed at four positions on lines extended from diagonals of the rectangular region in the central part of the glass substrate in which the microelectrodes are disposed. The reference electrodes are insulated from each other and from the microelectrodes. These reference electrodes 10 are also connected to the electric contacts 7 situated on four sides of the glass substrate by the conductive pattern 12 for wiring same as the microelectrodes 11. The reference electrodes 10 are formed in the same process as the microelectrodes 11, as mentioned below, but the size is generally significantly larger than that of the microelectrodes 11 being, e.g., a rectangle of about 200 microns in one side. Therefore, as compared with one of the microelectrodes 11 of about 50 microns square, the rectangular area is larger, preferably about 16 times larger, and, by this portion, the impedance of the reference electrodes 10 is smaller than the impedance of the microelectrodes 11.

The positions of the reference electrodes 10 are preferably on lines extending from the diagonals of the rectangular region in the central part of the glass substrate in which the microelectrodes 11 are disposed. The reference electrodes 10 in this variation are located about 6 mm from the center of the rectangular region. Said another way, they are placed at four corners of a square of about 8.5 mm in one side.

Figure 5:
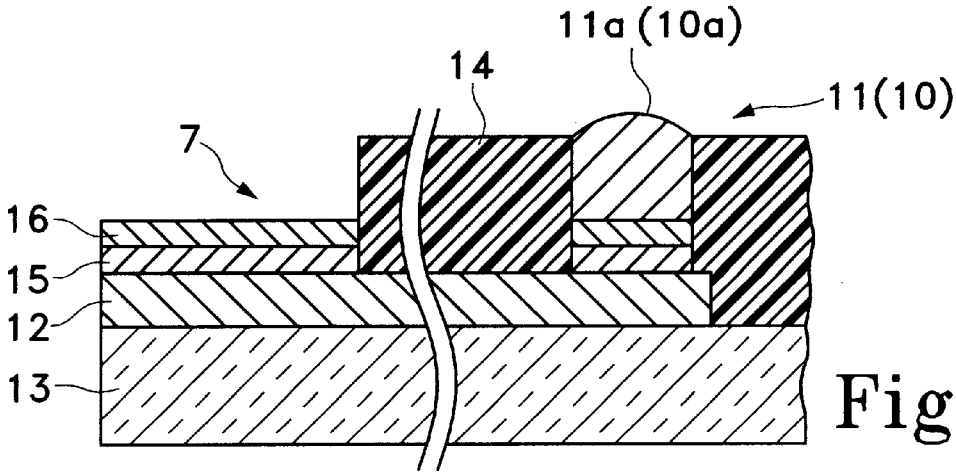
FIG. 5 is a schematic diagram of a section of a cell potential measuring electrode.

Moreover, as shown in FIG. 4, on each of the four sides of the glass substrate may be found 17 electric contacts 7. These electric contacts 7 are attached (one-by-one) to each of the 64 microelectrodes 11 and four reference electrodes 10 through the conductive pattern 12. The pitch of the 17 electric contacts is desirably spaced to the pitch of 1.27 mm of the universal connector. The manufacturing process of this integrated multiple electrode 2 is explained below by referring to the sectional view in FIG. 5. The depiction in FIG. 5, for the ease of explanation, is not to scale.

On the surface of a glass substrate 13, an ITO (indium tin oxide) film in a thickness of 150 nm is applied, and a conductive pattern 12 is formed by photo resist and etching. A 30 negative photosensitive polyimide film of about 1.4 microns in thickness is applied thereon, and an insulating film 14 is formed. On portions of the microelectrodes 11 (or alternatively reference electrodes 10) and electric contacts 7, the ITO film is exposed, and nickel plating 15 of 500 nm in thickness and gold plating 16 of 50 nm in thickness are then applied.

A polystyrene or glass cylindrical member 6 corresponding to a wall of about 22 mm in inside diameter, about 25 mm in outside diameter, and 8 mm in height may then be placed on the central part of the glass substrate by using a Silicone adhesive (see FIG. 2 and FIG. 4). A highly preferred adhesive is an RTV (Room Temperature Vulcanization) silicon rubber, particularly those which use an acid cure system. These produce a low level of toxicity because of the acetic acid produced during the cure step. Two useful varieties include KE42T (Shin-Etsu Silicon) and Silastic Medical Adhesive Silicon Type A (Dow Corning). A cylindrical wall member 6 is shown, but the wall may be oval to allow enhanced access to the sample. The wall member 6 is affixed in the center of the glass substrate. That is, in a state affixed with the central part of the rectangular region in which the 64 microelectrodes are disposed. In the region enclosed by this cylindrical member 6, the cells or tissues are cultivated. This cylindrical member 6 is filled, e.g., with an aqueous solution of 1 wt. % of chloroplatinic acid, 0.01 wt. % of lead acetate and 0.0025 wt. % of hydrochloric acid, and by passing a current of 20 $mA/cm^2$ for a minute, platinum blacks 11*a* (or alternatively, reference electrode platinum black 10*a*) are precipitated on the surfaces of the microelectrodes 11 and reference electrodes 10.

The region within the cylindrical member 6 is occasionally referred to as the "measuring region" which includes the area including both the microelectrodes 11 and reference electrodes 10. It is further within the scope of the invention that the reference electrodes be placed on the inner surface of the cylindrical member 6.

At one corner of the integrated multiple electrode 2, an indexing or arrow mark 17 showing the direction is provided. This arrow mark 17 can be formed in the same manufacturing process as the microelectrodes 11 and reference electrodes 10. However, the surface is coated with gold plating only, and platinum black is not formed. The length and width of the arrow mark 17 are both about 5 mm. Moreover, near one corner of the rectangular region of disposing the microelectrodes 1, a small indexing mark, e.g., a micro-mark 18 similar to the arrow mark is provided. This micro-mark 18 is not visible by the naked eye, but a same pattern as the arrow mark 17 is recognized in a magnified view by an optical observation device of the measuring apparatus, so that the direction, position, axes etc. may be identified. Like the arrow mark 17, the micro-mark 18 can be also formed in the same manufacturing process as the microelectrodes 11 and reference electrodes 10.

In FIG. 2, the integrated multiple electrode 2 is sandwiched between holders 3, 4.

Figure 6A:
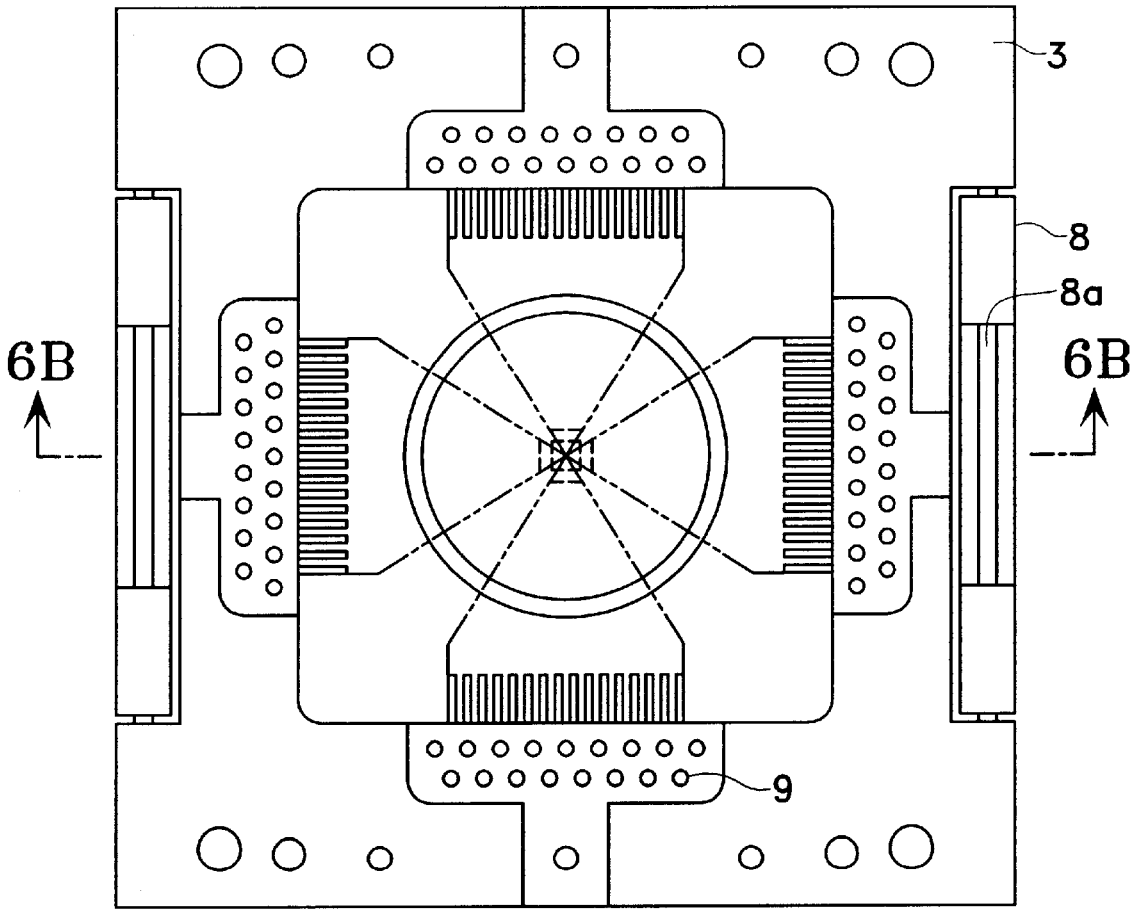
FIGS. 6(A) and 6(B) are respectively is a plan view and a side sectional view showing a state of fixing the cell potential measuring electrode by sandwiching with upper and lower holders.

An electrical connection is made in the same way. The holders 3, 4 are typically polymeric. The step portion is used to hold the edge of the integrated multiple electrode 2 and the rectangular opening are formed in the central part. The upper holder 3 is provided with a pair of fasteners 8 and 17 pieces×4 pairs of contact metal areas 9. A top view of the holders 3, 4 sandwiching and fixing the integrated multiple electrode 2 is shown in FIG. 6(A), its side view (section B—B) in FIG. 6(B), and its perspective back view in FIG. 7. As clear from these diagrams, the fastener 8 is supported by and rotates about shaft pins 8*a* on two confronting sides of the upper holder 3. As shown in FIG. 7, grooves 4*a* are formed in two confronting sides of the back side of the lower holder 4. Protrusions 8*b* of the fastener 8 are fitted in grooves 4*a* and the upper and lower holders 3, 4 are fixed firmly in a state of sandwiching the integrated multiple electrode 2.

Figure 8:
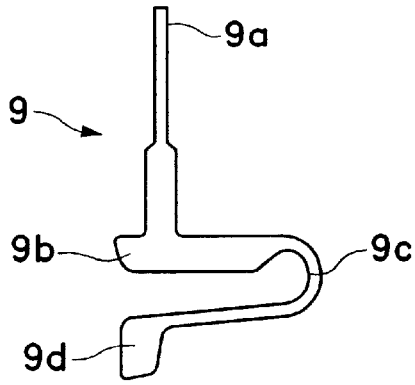
FIG. 8 is a side view of contact metal fittings provided in the upper holder.

A total of 68 contact metal fittings 9 provided on the upper holder 3 to correspond to the electric contacts 7 of the integrated multiple electrode 2 may be formed by processing elastic and conductive metal plates such as a Be/Cu spring alloy, plated with Ni and Au. The metal fittings 9 have a sectional shape as shown in FIG. 8. That is, it consists of a pin 9*a*, its base part 9*b*, and a movable contact part 9*d* extending from the base part 9*b* through a curved part 9*c*. In such structure, the movable contact part 9*d* can be elastically dislocated from the base part 9*b*. In the upper holder 3, holes for inserting the pin 9*a* of the contact metal fitting 9, and grooves for fitting the base part 9*b* are formed in 68 (17×4) positions.

Figure 6B:
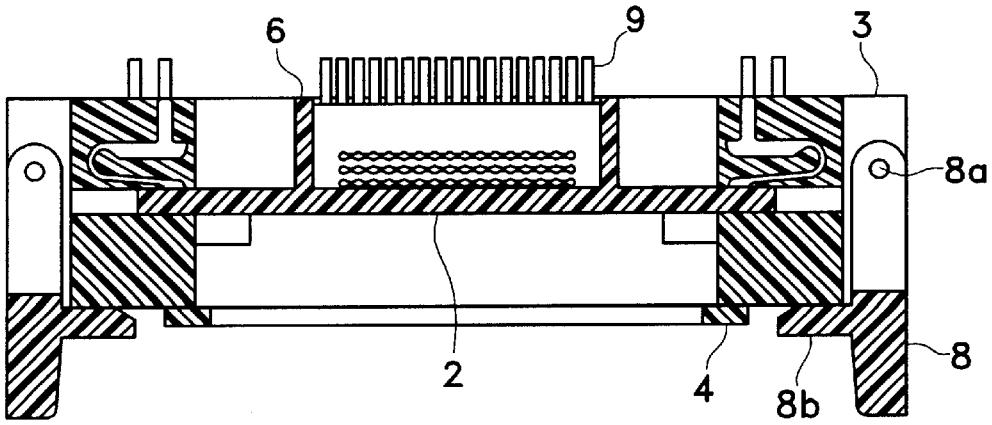
Figure 7:
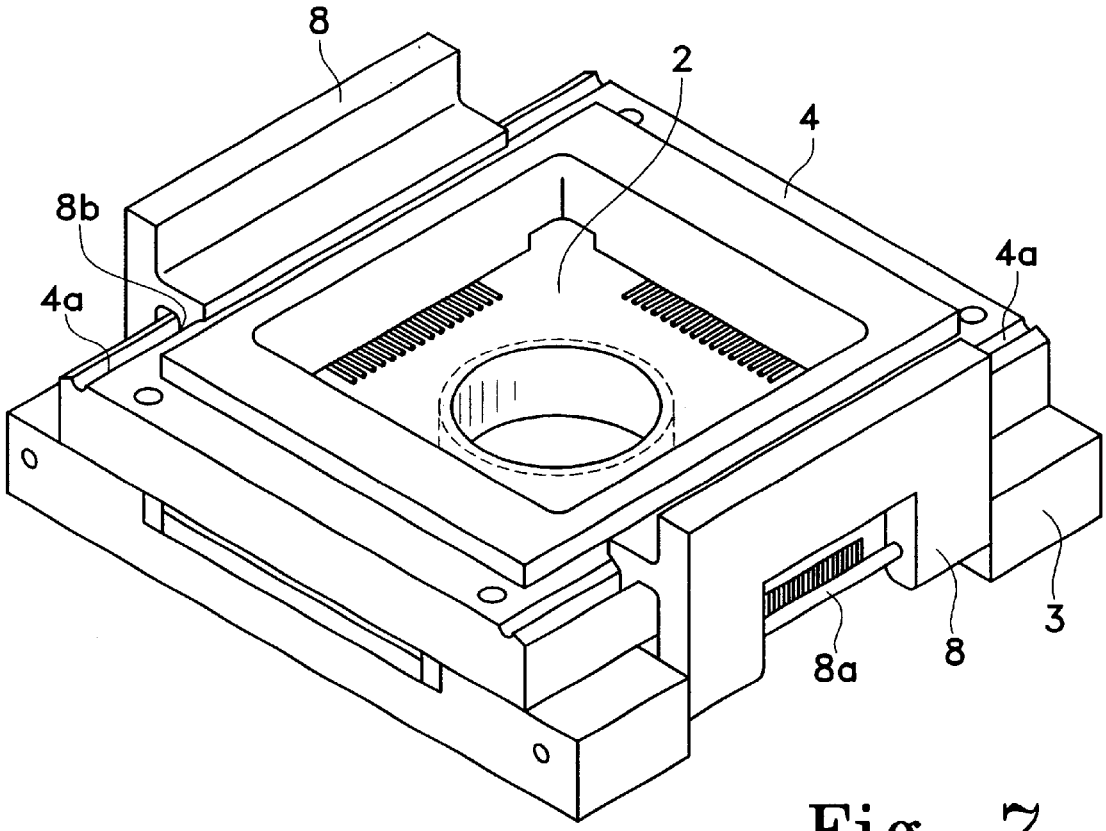
FIG. 7 is a perspective view of the cell potential measuring electrode and upper and lower holders in FIG. 6.

As shown in FIG. 2 and FIG. 6(B), with the contact metal fitting 9 inserted and fixed in the hole and groove, pin 9*a* projects from the upper holder 3. Contact metal fittings 9 are of two types which differ in the length of the base part 9*b*. The two sized fittings 9 are alternately disposed, 16 pins 9*a* projecting from the upper holder 3 are arranged in two zigzag rows. As mentioned later, these pins 9*a* are connected to the connectors mounted on the printed wiring board 5 for connection with the outside.

Movable contact part 9*d* of the contact metal fitting 9 projects from the lower side of the upper holder 3, when in contact metal fitting 9 is inserted and affixed in the hole and groove of the upper holder 3. With the holders 3, 4 fixed on both sides of the integrated multiple electrode 2, the movable contact part 9*d* of each contact metal fitting 9 contacts with the electric contact 7 of the integrated multiple electrode 2, and a specified contact pressure is given to the contact area by elastic deformation of the curved part 9*c*. In this way, the electric contacts 7 for connecting to the microelectrodes 11 and reference electrodes 10 of the integrated multiple electrode 2 through the conductive pattern 12 are electrically connected at a lower contact resistance (30 milliohms or less) as compared with that of the contact metal fittings 9.

As mentioned above, the holders 3, 4 firmly fixing the integrated multiple electrode 2 in a state of electric contact with the integrated multiple electrode 2 are electrically connected and affixed to the printed wiring board 5 as shown in FIG. 2. The electric connection from the microelectrodes 11 and reference electrode 10 of the integrated multiple electrode 2 to the conductive pattern 12, electric contacts 7 and contact metal fittings 9 is further connected to the cell potential measuring apparatus mentioned above through the printed wiring board 5. Handling of the integrated multiple electrode on the measuring apparatus is facilitated by use of the printed wiring board 5.

Also as shown in FIG. 2, printed circuit board 5 may be made up of, e.g., a glass epoxy two-sided substrate. Connectors 5*a* are provided at the back side of four positions on the circumference of the circular opening formed in the center of printed circuit board 5. Since 16 pins 9*a* projecting in two zigzag rows from the four positions on the surface of the upper holder 3 are inserted into the individual corresponding connectors 5*a,* the assembly of the integrated multiple electrode 2 and holders 3, 4 is fixed to the printed wiring board 5 and is connected electrically.

At both edges 5*b* of the printed wiring board 5, electric contacts of 2.54 mm pitch for both edge connectors may be found. These electric contacts and central connectors 5*a* are connected in the conductive pattern 5*c*. The inside row of the both connectors 5*a* is wired by the surface pattern, and the outside row by the back side pattern, respectively, and 34 each on both surface and back sides of both edges 5*b,* that is, a total of 68 electric contacts are formed. To make the mechanical fixing secure, the upper holder 3 may be affixed to the printed wiring board 5 by fastening with screws.

The reference electrodes 10 of the integrated multiple electrode 2 described by reference to FIG. 4. The reference electrodes 10 are usually immersed in the culture fluid as the reference potential for measuring the potential occurring in each microelectrode. Therefore, each microelectrode 11 is connected to an input of the amplifier 34 (FIG. 1), and the reference electrodes 10 are connected to the reference voltage terminals of each amplifier. The 64-channel amplifier is divided into four groups of 16 channels each, and each one of the four reference electrodes is commonly connected to the reference voltage terminal of one group for 16 channels.

First, as is clear from FIG. 4, it is preferred to position the four reference electrodes 10 on extensions of diagonals of the central rectangular region containing the microelectrodes 11. In general, this is a matter of convenience for pattern wiring. Moreover, in order to place the segments of cells or tissues easily so as to cover all of 64 microelectrodes and not to cover the four reference electrodes, the distance between the central rectangular region disposing the microelectrodes electrodes 11 and the reference electrodes 10 should be as large as reasonably possible. Moreover, by placing the four reference electrodes 10 at equal distances from the center of the rectangular region, the noise level occurring in each microelectrode is substantially uniform. Although the positions of the reference electrodes are closely specified above, the numerical values are not intended to be absolute, but are only intended to be guidelines.

The size of the reference electrodes 10 may be 4–64, preferably about 16, times the area of a microelectrode as mentioned above. As a result, the impedance is balanced between the measuring potential input side of the amplifier and the reference potential input side and the noise level is minimized. For instance, by forming the microelectrodes and reference electrodes in the same noted process and by setting the area of the reference electrode 16 times that of the microelectrode, the impedance of 16 microelectrodes and the impedance of one reference electrode responsible are nearly equal.

EXAMPLE

Figure 9:
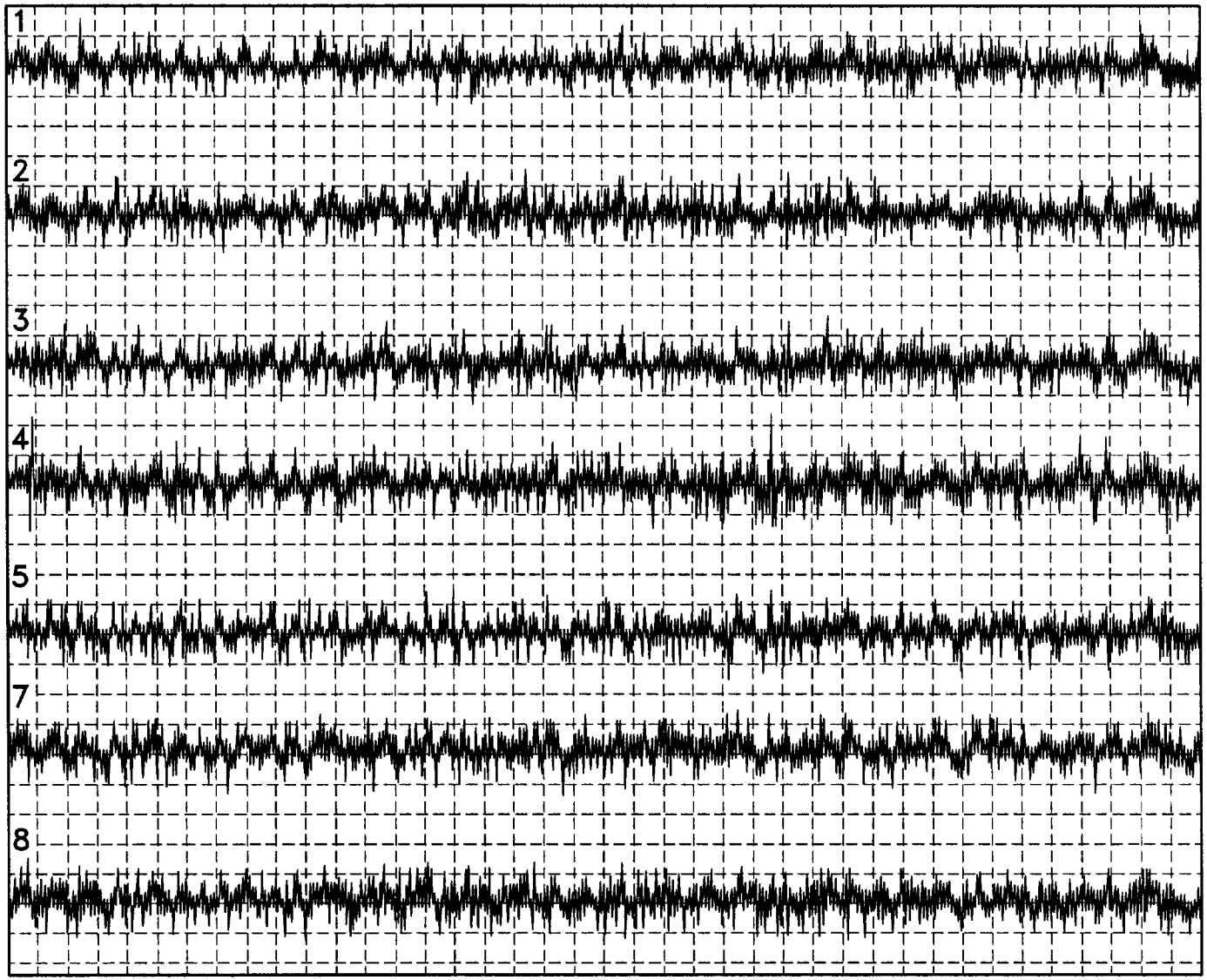
FIG. 9 is a waveform diagram showing noise level in the case of 50-micron square size of reference electrodes provided in the cell potential measuring electrode.
Figure 10:
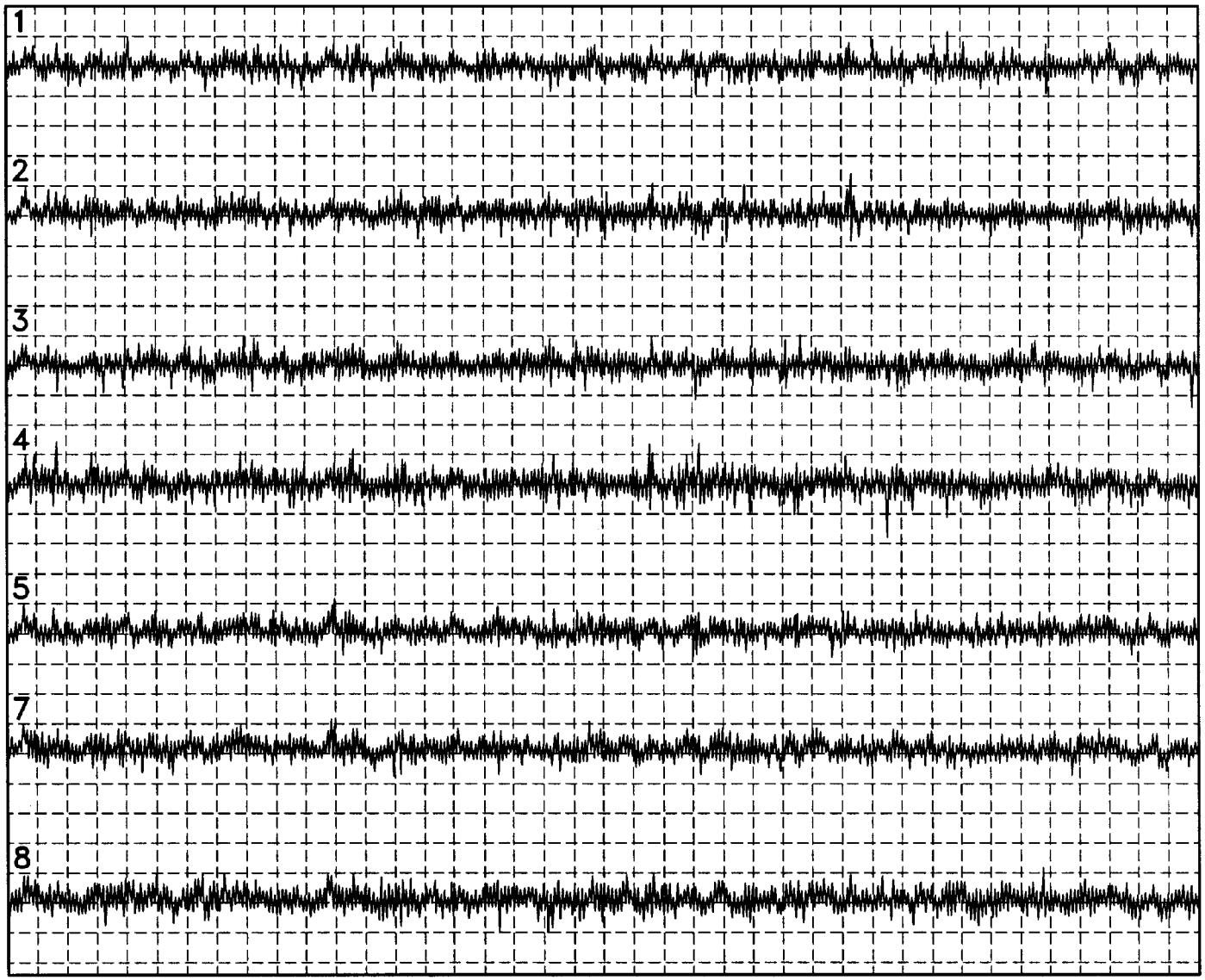
FIG. 10 is a waveform diagram showing noise level in the case of 50-micron square size of reference electrodes provided in the cell potential measuring electrode.

This Example shows the difference in noise level between a system including an integrated multiple electrode such as that discussed above and reference electrodes of 50 microns square and 200 microns square. FIG. 9 and FIG. 10 show those comparative noise levels.

Figure 11:
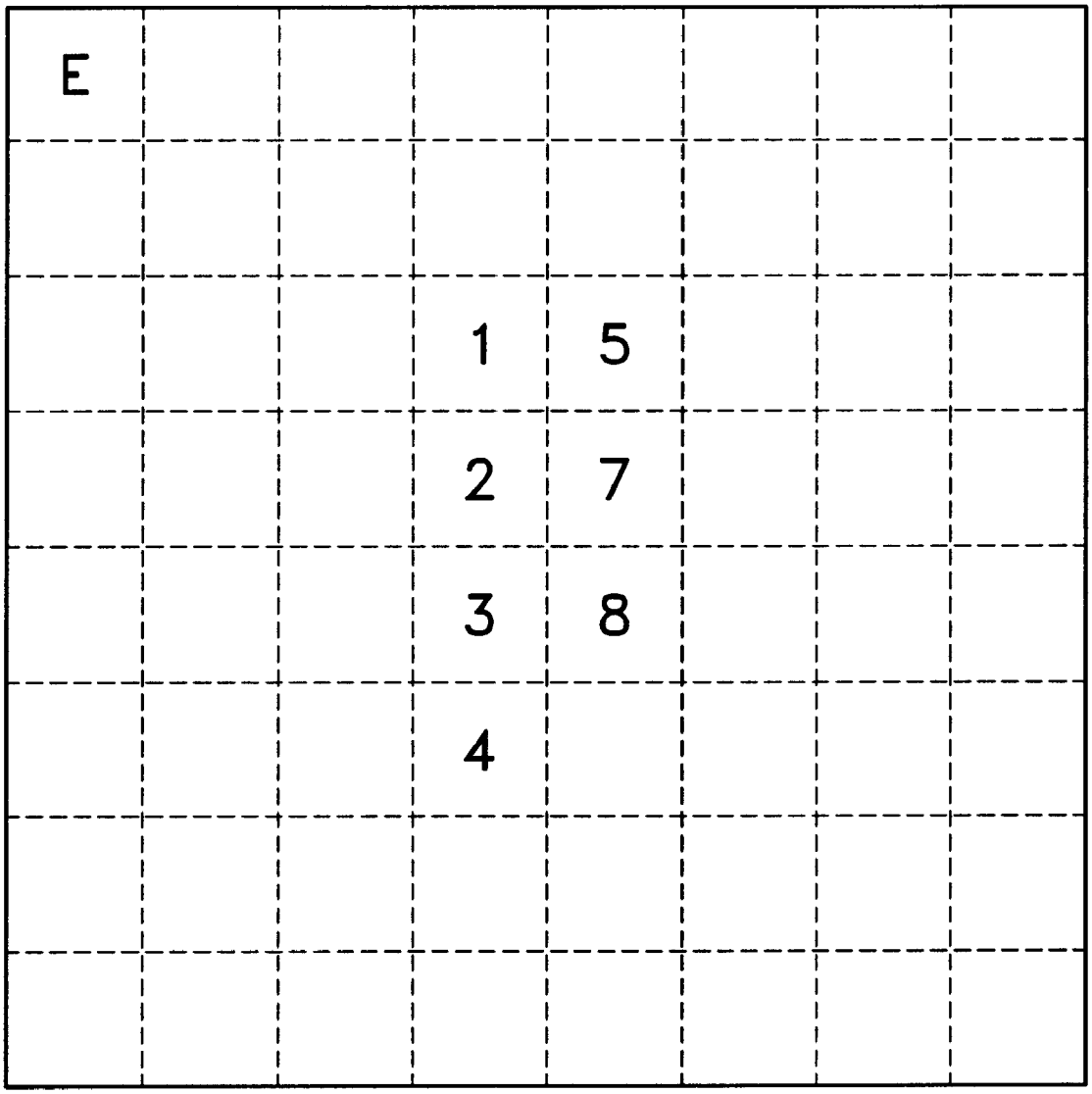
FIG. 11 is a waveform diagram showing noise level in the case of 200-micron square size of reference electrodes provided in the cell potential measuring electrode.
Figure 12:
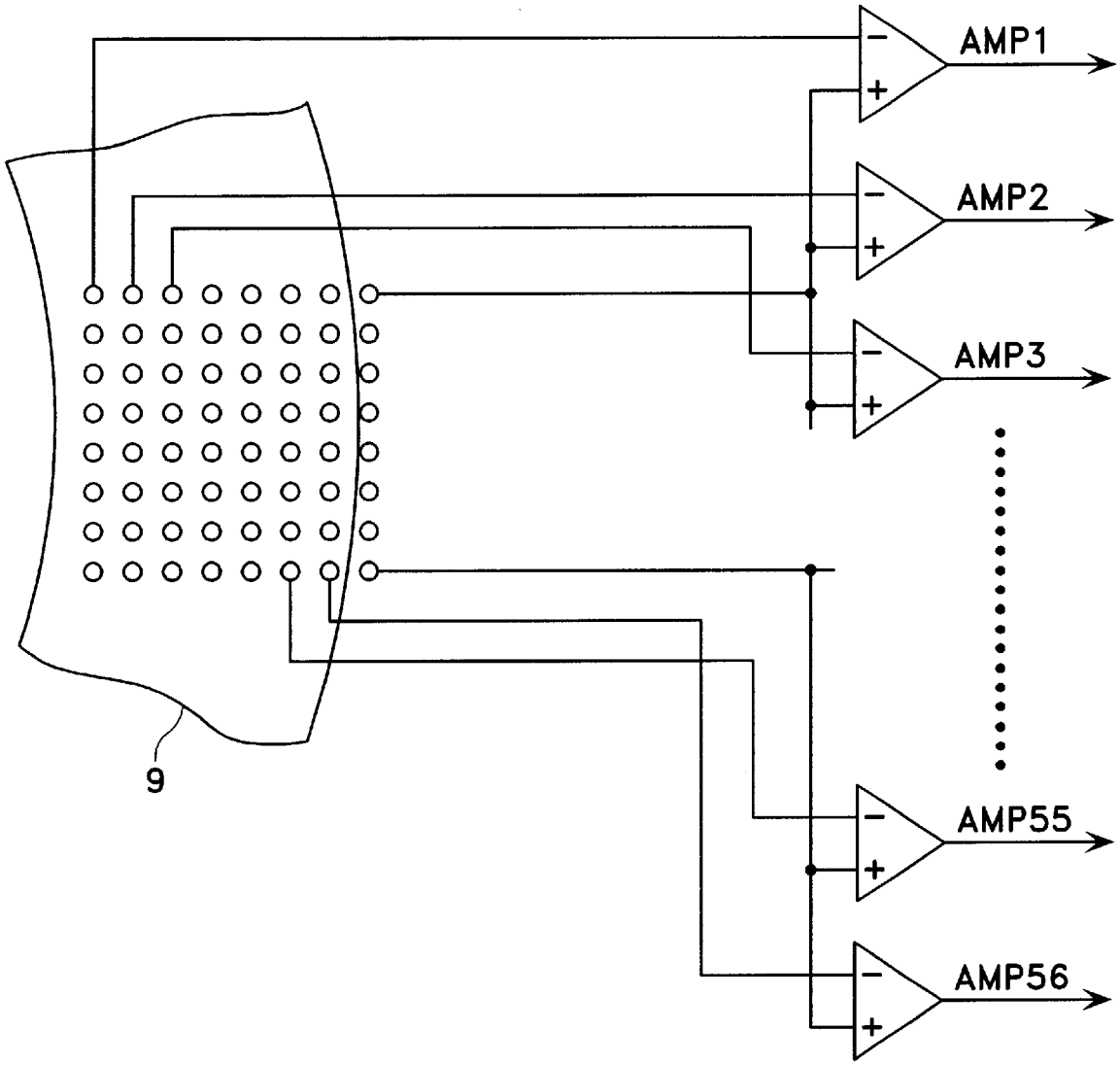
FIG. 12 is a block diagram showing an example of measuring method of cell potential by using a conventional cell potential measuring electrode.

We fabricated integrated multiple electrodes (such as shown in FIG. 4) having, respectively, reference electrodes of 50 microns square and reference electrodes of 200 microns square. The integrated multiple electrodes each had cylindrical members 6. The same culture medium as normally used in tissue culturing was placed inside the cylindrical members 6. To limit the resulting signal to the noise, no cell or tissue sample was placed on the microelectrodes. As shown in FIG. 11, of the 64 microelectrodes, the central seven sites (channels I to 5, 7, 8) were measured.

FIG. 9 shows the noise waveform of the reference electrodes in 50 microns square, and FIG. 10, 200 microns square. In each diagram, the voltage on the axis of ordinates is 0.02 mV/div, and the time on the axis of absicassas is 5.0 ms/div. As clear from comparison between FIG. 9 and FIG. 10, the noise level is clearly smaller when the reference electrodes are 200 microns square (FIG. 10) as compared to reference electrodes with 50 microns square (FIG. 9). Incidentally, as described in relation to the prior art, by using one of the 64 microelectrodes as the reference electrode to be responsible for 16 microelectrodes, the noise level was as large as in FIG. 9.

As described herein, according to the cell potential measuring electrode and apparatus of the invention, the noise effect is small, and if positioning when setting the segments of cells or tissues to be measured is not very precise, all microelectrodes are effectively utilized, and potentials at multiple points can be measured simultaneously.

We claim as our invention:

1. A cell potential measuring electrode assembly suitable for measuring electrical potential in a neural sample comprising:

a. a plurality of measurement microelectrodes insulated from each other and located on an insulating substrate in a measuring region, b. a plurality of reference electrodes located on said insulating substrate and isolated from each other in said measuring region, each of said plurality of reference electrodes having an impedance smaller than said each of said measurement electrodes when measured in an electrolyte covering said measuring region at 1 kHz, 50 mv.

2. The cell potential measuring electrode assembly of claim 1 wherein the area of each of the plurality of reference electrodes is larger than the area of each of the plurality of measurement microelectrodes.

3. The cell potential measuring electrode assembly of claim 2 wherein the area of each of the plurality of reference electrodes is 4 to 25 times the area of each of plurality of measurement microelectrodes.

4. The cell potential measuring electrode assembly of claim 2 wherein the area of said each of plurality of measurement microelectrodes is $4\times10^2$ to $4\times10^4$ $\mu m^2$ and the area of each of the plurality of reference electrodes is $64\times10^2$ to $64\times10^4$ $\mu m^2$.

5. The cell potential measuring electrode assembly of claim 1 wherein each of the plurality of measurement microelectrodes are situated in an array in said measuring region.

6. The cell potential measuring electrode assembly of claim 5 wherein 64 microelectrodes are disposed in eight rows and eight lines at central pitches of 100 to 450 microns.

7. The cell potential measuring electrode assembly of claim 1 wherein each of the plurality of measurement microelectrodes and each of the plurality of reference electrodes are connectable to a position outside of the measuring region.

8. The cell potential measuring electrode assembly of claim 1 wherein the measuring region is surrounded by a wall.

9. The cell potential measuring electrode assembly of claim 8 wherein the wall is circular.

10. The cell potential measuring electrode assembly of claim 8 wherein the wall is oval.

11. A cell potential measuring electrode comprising plural microelectrodes disposed on an insulating substrate, a conductive pattern for wiring of said microelectrodes, an electric contact connected to the end of said conductive pattern, an insulating film covering the surface of said conductive pattern, and a wall enclosing the region including the microelectrodes on the surface of said insulating film, being a cell potential measuring electrode for use in measurement of electrophysiological activities while cultivating cells or tissues in a region enclosed by said wall, wherein reference electrodes having a smaller impedance than the impedance of said microelectrodes are respectively disposed at plural positions located on said insulating substrate in the region enclosed by said wall and at a specific distance from the region of disposition of said microelectrodes, electric contacts are further connected between the conductive pattern for wiring of each reference electrode and the end of said conductive pattern, and the surface of the conductive pattern for wiring of said reference electrodes is covered with said insulating film.

12. A cell potential measuring electrode of claim 11, wherein said plural reference electrodes are disposed at nearly equal distance from the region of disposition of said plural microelectrodes and at intervals of nearly equal angle.

13. A cell potential measuring electrode of claim 12, wherein said plural microelectrodes are disposed in a matrix in a rectangular region, and four of said reference electrodes are provided on an extension of diagonals of said rectangular region.

14. A cell potential measuring electrode of claim 13, wherein said microelectrodes are 0.8 to 3.3 mm in one side of a rectangular region in matrix arrangement, and said four reference electrodes are disposed at four corners of a rectangular form of 5 to 15 mm in one side.

15. A cell potential measuring electrode of claim 14, wherein 64 microelectrodes are disposed in eight rows and eight lines at central pitches of 100 to 450 microns.

16. A cell potential measuring electrode of claim 11, wherein the area of said reference electrodes is 4 to 25 times the area of said microelectrodes.

17. A cell potential measuring electrode of claim 16, wherein the area of said reference electrodes is 16 times the area of said microelectrodes.

18. A cell potential measuring electrode of claim 11, wherein the area of said microelectrodes is $4\times10^2$ to $4\times10^4$ $\mu m^2$ and the area of said reference electrodes is $64\times10^2$ to $64\times10^4$ $\mu m^2$.

19. A cell potential measuring electrode of claim 11, wherein said microelectrodes and said reference electrodes are formed of a same material.

20. A cell potential measuring electrode of claim 19, wherein said microelectrodes and said reference electrodes are formed by layering nickel plating, gold plating, and platinum black on an indiun-tin oxide film.

21. A cell potential measuring electrode of claim 11, wherein said insulating substrate is nearly square, and plural electric contacts connected to the end of said conductive pattern are distributed and disposed in four sides of said insulating substrate.

22. A cell potential measuring electrode of claim 11, wherein indexing micro-marks for visually recognizing direction when magnified are provided near the regions of disposition of said microelectrodes.

23. A cell potential measuring apparatus comprising:

a cell placement device having a cell potential measuring electrode in any one of claims 11 to 22, and a contact metal for contacting with its electric contact, and including an electrode holder for fixing said insulating substrate by sandwiching from above and beneath, a signal processor connected electrically to said cell placement device for processing voltage signals generated between each microelectrode and reference electrode of said cell potential measuring electrode by the activity of cells or tissues cultivated in a region enclosed by a wall, and an optical device for magnifying and observing optically the cells or tissues cultivated in the region enclosed by said wall.

24. A cell potential measuring apparatus of claim 23, further comprising an image memory device for storing the magnified image obtained by said optical device.

* * * * *